United States Patent [19]
Nielson et al.

[11] Patent Number: 5,646,019
[45] Date of Patent: Jul. 8, 1997

[54] METHOD FOR PRODUCING PRIMED NUCLEIC ACID TEMPLATES

[75] Inventors: Kirk B. Nielson, San Diego; Eric J. Mathur, Solana Beach, both of Calif.

[73] Assignee: Stratagene, La Jolla, Calif.

[21] Appl. No.: 224,981

[22] Filed: Apr. 7, 1994

Related U.S. Application Data

[63] Continuation of Ser. No. 425,867, Oct. 24, 1989, abandoned.

[51] Int. Cl.$^6$ .................................................. C12P 19/34
[52] U.S. Cl. ................................... 435/91.5; 435/91.1
[58] Field of Search ...................... 435/91.1; 935/91.1, 935/91.5, 77.78

[56] References Cited

U.S. PATENT DOCUMENTS

| | | | |
|---|---|---|---|
| 4,505,685 | 3/1985 | Zapolski et al. | 435/6 |
| 4,683,195 | 7/1987 | Mullis et al. | 435/6 |
| 4,889,818 | 12/1989 | Gelfand et al. | 435/6 |
| 4,994,372 | 2/1991 | Tabor et al. | 435/6 |

OTHER PUBLICATIONS

Hong, Bioscience Reports 2:907–912 (1982).
Muniyappa et al. PNAS. USA 81:2757–2761 (May 1984).
Beck, B.N. and Ho, S.N., "Increased specificity of PCR-amplified products by size-fractionation of restriction enzyme-digested template genomic DNA," *Nucleic Acids Research* 16(18):9051 (1988).
Haqqi, T.M. et al., "Specific amplification with PCR of a refractory segment of genomic DNA," *Nucleic Acids Research* 16(24):11844 (1988).
Chase, J.W. and Williams, K.R., "Single-stranded DNA binding proteins required for DNA replication," *Annu. Rev. Biochem* 55:103–36 (1986).
Chase, J.W. et al., "Characterization of the *Escherichia coli* SSB–113 mutant single–stranded DNA–binding protein. Cloning of the gene, DNA and protein sequence analysis, high pressure liquid chromatography peptide mapping, and DNA-binding studies,"*Journal of Biological Chemistry* 259(2):805–814 (1984).

Coleman, J.E. and Oakley, J.L., "Physical chemical studies of the structure and function of DNA binding (helix–destabilizing) proteins," *CRC Crit. Rev. Biochem.* 7(3):247–289 (1980).
LaDuca, R.J. et al., "Site-specific pausing of deoxyribonucleic acid synthesis catalyzed by four forms of *Escherichia coli* DNA polymerase III," *Biochemistry* 22(22):5177–5188 (1983).
Huberman J.A. et al., "Stimulation of T4 bacteriophage DNA polymerase by the protein product of T4 gene 32," *J. Mol. Biol.* 62(1):39–52 (1971).
Kaspar, P. et al., "An improved double stranded DNA sequencing method using gene 32 protein," *Nucleic Acids Research* 17(9): 3616 (1989).
Studier, F.W., "A strategy for high–volume sequencing of cosmid DNAs: random and directed priming with a library of oligonucleotides," *Proc. Natl. Acad. Sci. USA* 86(18):6917–6921 (1989).
Sommer, R. and Tautz, D., "Minimal homology requirements for PCR primers," *Nucleic Acids Research* 17(16):6749 (1989).
Christiansen, C. and Baldwin, R.L., "Catalysis of DNA reassociation by the *Escherichia coli* DNA binding protein: A polyamine–dependent reaction," *J. Mol. Biol.* 115(3):441–454 (1977).
Lindberg, G. et al., "Purification and characterization of the coliphage N4–coded single–stranded DNA binding protein," *J. Biol. Chem.* 264(21): 12700–12708 (1989).
Muta Gene M13 *in vitro* mutagenesis kit instructions version #189 89–0096, p. 34 Bio-Rad Laboratories, Richmond, CA.

*Primary Examiner*—Stephanie W. Zitomer
*Attorney, Agent, or Firm*—Albert P. Halluin, Esq.; Pennie & Edmonds

[57] ABSTRACT

The present invention relates to an improved method for producing primed nucleic acid templates. Specifically, it relates to a method, compositions and kits therefor, of increasing the specificity of primer extension reactions by hybridizing primer to template in the presence of single-stranded nucleic acid binding protein.

16 Claims, 3 Drawing Sheets

FIG. 2
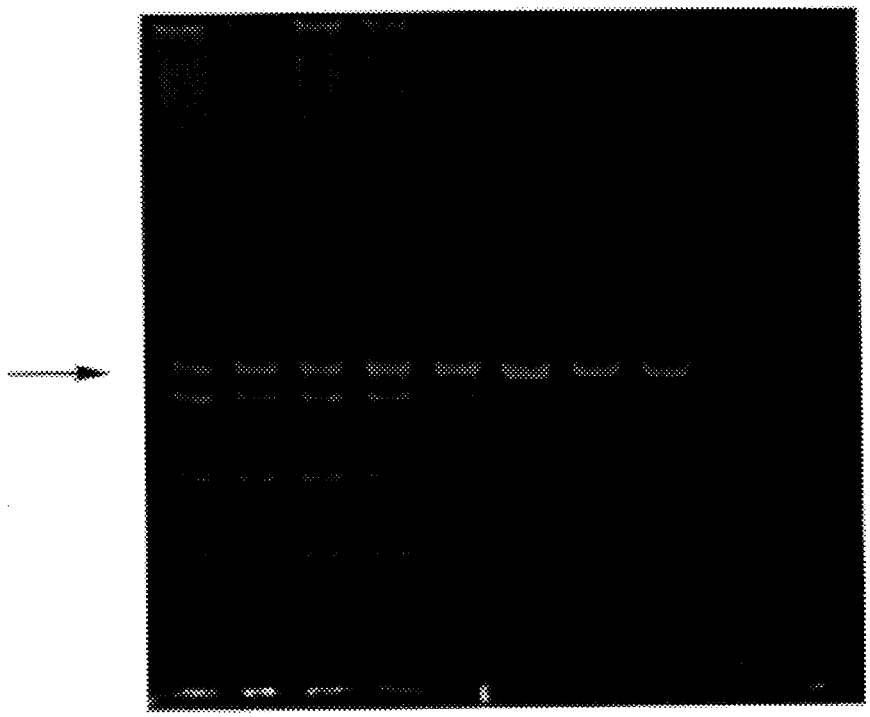
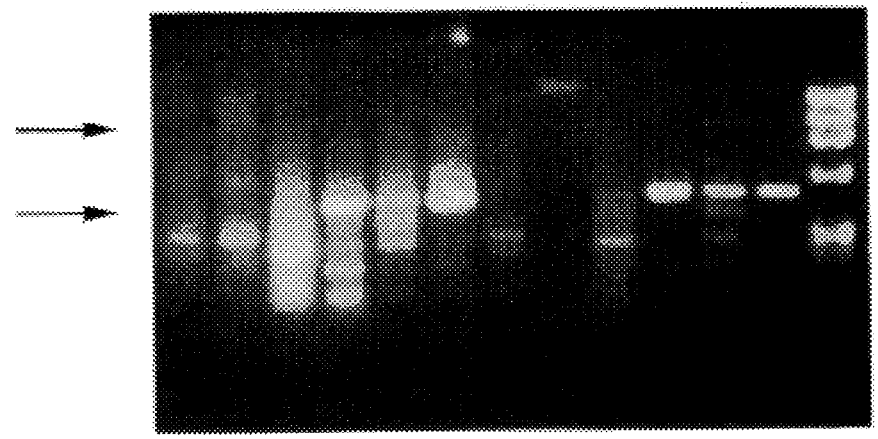
FIG. 3

METHOD FOR PRODUCING PRIMED NUCLEIC ACID TEMPLATES

DESCRIPTION

This is a continuation of application Ser. No. 07/425,867, filed Oct. 24, 1989, now abandoned.

TECHNICAL FIELD

The present invention relates to an improved process for producing primed nucleic acid templates. More specifically, it relates to a method of increasing the specificity of polynucleotide synthesis via primer extension reactions by hybridizing primer to template in the presence of a single-stranded nucleic acid binding protein.

BACKGROUND OF THE INVENTION

Primed templates are nucleic acids comprised of two nucleic acid strands of unequal length bound together to form a substrate for polynucleotide synthesis. Primed templates are used in a wide variety of molecular biological techniques, including gene cloning, in vitro gene mutagenesis, nucleic acid amplification, nucleic acid detection, and the like.

Primed templates are typically produced by hybridizing (annealing) a primer to a target nucleotide sequence on the template that is complementary to the sequence of the primer. The fidelity of hybridization reactions of primer with template is known to vary depending on a variety of factors, including temperature, complexity of the template, and the like. Generally, greater template length and higher hybridization temperatures each contribute to increased mismatching between primer and template resulting in inappropriately and undesirably primed template.

Inappropriately primed template is the major cause of undesirable (background) primer extension reaction products in primer extension reactions. This is particularly the case in the polymerase chain reaction (PCR) method for amplifying specific nucleic acid sequences. See, for example, Beck et al, *Nuc. Acid Res.*, 16:9051 (1988); and Haqqi et al, *Nuc. Acid Res.*, 16:11844 (1988).

In PCR, specific nucleic acid sequences are amplified using a chain reaction in which primer extension products are produced using primed nucleic acid templates. The product of each primer extension reaction specifically anneals with a primer and the resulting primed template acts as a substrate for further primer extension reactions. PCR is particularly useful in detecting nucleic acid sequences which are initially present in only very small amounts. However, the utility of PCR is often hampered by high levels of background primer extension reaction products due to primer/template mismatching. The procedure for conducting PCR has been extensively described. See U.S. Pat. No. 4,683,195 and No. 4,683,202 both to Mullis et al.

Single-stranded nucleic acid binding proteins (SSB) have been characterized in some detail and include such members as the *E. coli* single-stranded binding protein (Eco SSB), T4 gene 32 protein (T4 gp32), T4 gene 44/62 protein, T7 SSB, coliphage N4 SSB, adenovirus DNA binding protein (Ad DBP or Ad SSB), and calf thymus unwinding protein (UP1). Chase et al, *Ann. Rev. Biochem.*, 55:103–36 (1986); Coleman et al, *CRC Critical Reviews in Biochemistry*, 7(3) :247–289 (1980); Lindberg et al, *J.Biol. Chem.*, 264: 12700–08, 1989; and Nakashima et al, *FEBS Lett.* 43: 125, 1974.

Eco SSB is an SSB that increases the fidelity of DNA replication and stimulates *E. coli* DNA polymerases II and III but not polymerase I or T4 DNA polymerase. Chase et al, *Ann. Rev. Biochem.*, 55:103–36 (1986). Eco SSB has been shown to relieve pausing by DNA polymerase III assemblies at regions of secondary structure [(LaDuca et al, *Biochem.*, 22:5177–87 (1983)] and in vitro studies of RecA-mediated reactions suggest that SSB affects ssDNA by removing secondary structures. Muniyappa et al, *Proc. Natl. Acad. Sci. USA*, 81:2257–61 (1984).

T4 Gene 32 protein is an SSB coded for by gene 32 of bacteriophage T4. One of its functions is to assist T4 DNA polymerase synthesis across regions of secondary structure in a single-stranded template. Huberman et al, *J.Mol.Biol.*, 62: 39–52 (1971). It has also been used in an in vitro mutagenesis reaction to promote uninterrupted synthesis from template by addition of gene 32 protein to the template after a mutagenized primer is annealed but before polymerization. Muta-Gene M13 in vitro mutagenesis kit instructions, version #189 89–0096, p.34, Bio-Rad Laboratories, Richmond, Calif.

SSB therefore has traditionally been viewed as functioning by minimizing secondary structure in ssDNA and thereby facilitating enzyme passage (processivity) along the DNA template. In this context, SSB has been used in a variety of ways based on this property of SSB.

Zapoliski et al, in published PCT Patent Application No. WO85/05685, describe the use of Eco SSB in combination with *E. coli* RecA protein and ATP to form a hybridization mixture having the capacity to stimulate the transfer of ssDNA to homologous duplexes. The Zapoliski disclosure indicates that a cooperative binding between Eco SSB and the ssDNA increases the homologous pairing mediated by RecA.

Kaspar et al, *Nuc. Acids Res.*, 17:3616 (1989) describes the use of T4 gp32 in the primer annealing and the primer extension steps of a dsDNA sequencing procedure. The Kaspar disclosure states that adding T4 gp32 allows Klenow enzyme to read through a region that previously caused termination, which suggests that the utility of T4 gp32 in a sequencing protocol was in reducing secondary structure to allow the polymerase to continue down the template.

BRIEF SUMMARY OF THE INVENTION

It has now been discovered that the presence of a single-stranded nucleic acid binding protein (SSB) decreases the amount of nonspecific primer extension products from primed templates.

This discovery has broad application to all procedures involving the production of primed template by nucleic acid hybridization. Particularly useful is the application of the discovery to methods in which a specific nucleotide sequence is amplified, such as by polymerase chain reaction, because the increased specificity of primer to template hybridization makes the procedure unexpectedly more sensitive.

Thus, the present invention contemplates a method of preparing a primed template comprising the steps of (a) forming a nucleic acid hybridization reaction admixture by admixing effective amounts of (i) a primer nucleic acid capable of specifically hybridizing to a template nucleic acid to form a substrate for polynucleotide synthesis, (ii) the template nucleic acid, (iii) an isolated SSB, and (iv) a divalent cation; and (b) maintaining said nucleic acid hybridization reaction admixture under hybridizing conditions for a time period sufficient for said primer nucleic acid to specifically bind said template nucleic acid, thereby forming said primed template. Preferably the SSB is Eco SSB, T4 gene 32 protein, or T7 SSB and more preferably is Eco SSB. It is also preferred that SSB is present in an effective amount in the range of 1 ng to 10 ug per 100 ng of template nucleic acid. In addition, it is preferred that the divalent cation be $Mg^{++}$, $Mn^{++}$, $Ca^{++}$ or $Zn^{++}$, and more preferably $Mg^{++}$ at an effective concentration of 15 mM.

In another embodiment the invention contemplates a method of preparing a strand of nucleic acid having a nucleotide sequence complementary to a template nucleic acid comprising the steps of (a) forming a primer extension reaction admixture by admixing the template nucleic acid with an effective amount of (i) a polynucleotide synthesis primer having a nucleotide sequence substantially complementary to a portion of the template nucleic acid, (ii) an isolated SSB, (iii) a divalent cation, and (iv) an enzyme capable of inducing polynucleotide synthesis in the presence of a primed template; and (b) maintaining the primer extension reaction admixture under polynucleotide synthesizing conditions for a time period sufficient for the enzyme to produce a primer extension product, thereby producing the strand of nucleic acid. Preferably the SSB is Eco SSB and the divalent cation is $Mg^{++}$, $Mn^{++}$, $Ca^{++}$ or $Zn^{++}$.

Another embodiment contemplates a method of amplifying a specific nucleic acid sequence present in a sample containing a double-stranded nucleic acid molecule comprising the steps of: (a) separating the strands of the double-stranded nucleic acid molecule to form single-stranded templates; (b) treating the single-stranded templates with the following in amounts effective to induce polynucleotide synthesis under polynucleotide synthesizing conditions: (i) primers that are selected so as to be substantially complementary to portions of the different strands of the specific double-stranded sequence to hybridize therewith such that an extension product synthesized from one primer, when it is separated from its template nucleic acid strand, can serve as a template for synthesis of the extension product of the other primer, (ii) an isolated SSB, (iii) a divalent cation, and (iv) an enzyme capable of producing primer extension products from the single-stranded templates, wherein the treatment is conducted under conditions such that the primers hybridize to the specific sequences and an extension product of each primer is synthesized by the action of the enzyme, said product being complementary to each single-stranded template; (c) separating the primer extension products formed in step (b) from the templates on which they are synthesized to produce single-stranded molecules; and (d) treating the single-stranded molecules produced in step (c) with effective amounts of the primers, SSB, divalent cation and enzyme of step (b) under conditions such that a primer extension product is synthesized using the single-stranded molecules formed in step (c) as a template. Preferably the SSB is Eco SSB, T4 gene 32 protein, or T7 SSB, and more preferably is the heat-stable SSB, Eco SSB. In addition, a preferred enzyme is Klenow fragment, Taq DNA polymerase, recombinant Taq DNA polymerase, T7 DNA polymerase, modified T7 DNA polymerase or T4 DNA polymerase, and more preferably is a heat-stable DNA polymerase such as Taq DNA polymerase.

In another embodiment the invention contemplates a composition for use in a polymerase chain reaction to amplify a specific nucleic acid sequence comprising an isolated SSB, a divalent cation and two polynucleotide primers that are selected so as to be sufficiently complementary to different strands of a duplex DNA containing the specific nucleic acid sequence as to hybridize therewith such that an extension product synthesized from one primer, when it is separated from its complementary nucleic acid strand, can serve as a template for synthesis of the extension product of the other primer, and wherein the SSB and primers are present in amounts effective to support a polymerase chain reaction.

A related embodiment contemplates a composition for amplifying a specific nucleic acid sequence in a double-stranded nucleic acid form comprising the following components in an amount sufficient for at least one assay: (a) an isolated SSB, (b) a divalent cation, (c) a nucleic acid polymerase, and (d) two polynucleotide primers that are selected so as to be sufficiently complementary to different strands of the double stranded nucleic acid containing the specific nucleic acid sequence to hybridize therewith such that an extension product synthesized from one primer, when it is separated from its complementary nucleic acid strand, can serve as a template for synthesis of the extension product of the other primer.

BRIEF DESCRIPTION OF THE DRAWINGS

In the drawings forming a portion of this disclosure:

FIG. 1A shows the results of a PCR amplification conducted in the absence of Eco SSB. FIG. 1B shows the results of a PCR amplification under the same conditions as FIG. 1A except that Eco SSB was included in the hybridization and primer extension reaction mixtures at 2.5 ug/ml.

FIG. 2 illustrates the range of effectiveness of an SSB protein for improving a PCR-based specific nucleic acid detection system when conducted as described in Example 2. Primer extension products were produced in the presence of varying amounts of Eco SSB, and were analyzed on 6% acrylamide gels as described in FIG. 1. The amount of Eco SSB added per 100 ul of PCR mixture was: 10 ng (lane 1), 50 ng (lane 2), 100 ng (lane 3), 250 ng (lane 4), 500 ng (lane 5), 1 ug (lane 6), 2 ug (lane 7), 5 ug (lane 8), 10 ug (lane 9), and zero ug (lane 10). The arrow indicates the position of the band representing an amplified nucleic acid fragment that contains the specifically primed nucleic acid sequence. All other bands are the result of non-specific primer hybridization. Lane 9 lacks primer extension products because of improper thermal cycling in that reaction well of the thermal cycler apparatus, or because 10 ug of Eco SSB may inhibit PCR.

FIG. 3 illustrates an analysis of hybridization stringency in a PCR-based detection system when conducted as described in Example 2. Primer extension products produced by PCR using either a 42C (lanes 1–6) or 54C (lanes 7–12) annealing temperature were analyzed as described in FIG. 1. PCR was conducted in the presence (+) or absence (−) or 2.5 ug Eco SSB per ml PCR mixture. Human genomic DNA was hybridized with primers pr 886 and pr 887 (lanes 1, 2, 7 and 8), and lambda transgene mouse genomic DNA (lanes 3–6 and lanes 9–12) was hybridized with an 18-mer primer pair, pr 737 and pr 738 (lanes 3, 4, 9 and 10), or with a 23-mer primer pair, pr 4266 and pr 19012 (lanes 5, 6, 11 and 12) in the PCR method. The upper arrow indicates the position of the 1800 bp specifically amplified nucleic acid fragment, and the lower arrow indicates the position of the 520 bp specifically amplified nucleic acid fragment. All other bands are the result of non-specific primer hybridizations. Lane M contains the same molecular weight markers as shown in FIG. 1.

DETAILED DESCRIPTION OF THE INVENTION

A. Definitions

Figure 1:
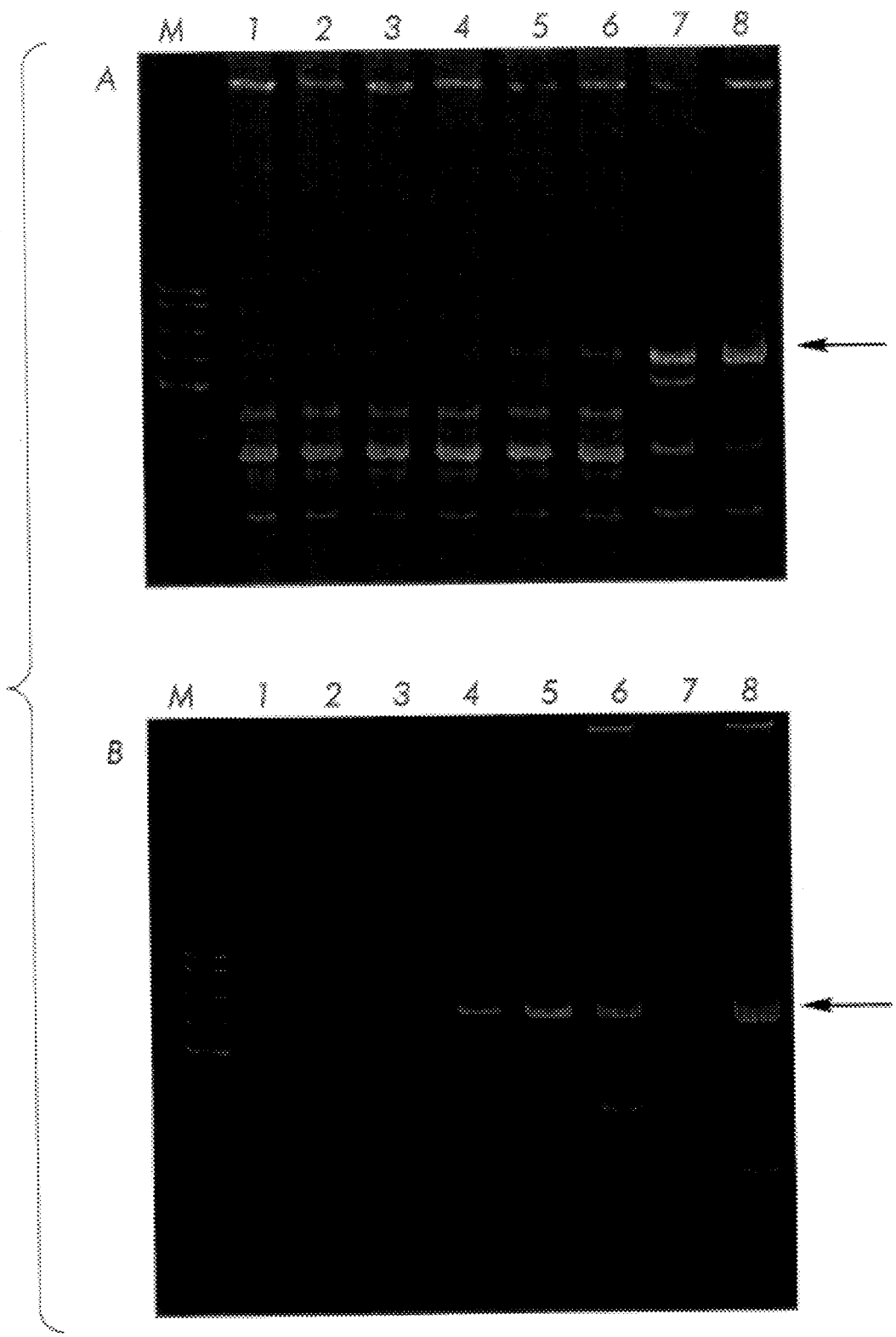
FIGS. 1A and 1B illustrate the sensitivity of a PCR amplification and detection system for specific nucleic acids when conducted as described in Example 2. Primer extension products produced by PCR were analyzed by electrophoresis on 6% acrylamide gels, after individual reaction mixtures were produced containing the following amounts of lambda transgene mouse genomic DNA: 1 pg (lane 1), 10 pg (lane 2), 100 pg (lane 3), 1 ng (lane 4) 10 ng (lane 5), 50 ng (lane 6), 100 ng (lane 7) and 1 ug (lane 8). The arrow indicates the position of the band representing an amplified nucleic acid fragment that contains the specifically primed nucleic acid sequence. All other bands are the result of non-specific primer hybridization. Lane M contains molecular weight markers produced from a Hinf I restriction endonuclease digest of bacteriophage phi X174 DNA.

Nucleotide: a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose it is referred to as a nucleotide. A sequence of operatively linked nucleotides is typically referred to herein as a "base sequence" or "nucleotide sequence", and is represented herein by a formula whose left to right orientation is in the conventional direction of 5'-terminus to 3'-terminus.

Duplex DNA: A double-stranded nucleic acid molecule comprising two strands of substantially complementary polynucleotide hybridized together by the formation of a hydrogen bond between each of the complementary nucleotides present in a base pair of the duplex. Because the nucleotides that form a base pair can be either a ribonucleotide base or a deoxyribonucleotide base, the phrase "duplex DNA" refers to either a DNA-DNA duplex comprising two DNA strands (ds DNA), or an RNA-DNA duplex comprising one DNA and one RNA strand.

Base Pair (bp): a partnership of adenine (A) with thymine (T), or of cytosine (C) with guanine (G) in a double stranded DNA molecule. In RNA, uracil (U) is substituted for thymine.

Nucleic Acid: a polymer of nucleotides, either single or double stranded.

Gene: a nucleic acid whose nucleotide sequence codes for a RNA or polypeptide. A gene can be either RNA or DNA.

Complementary Bases: nucleotides that normally pair up when DNA or RNA adopts a double stranded configuration.

Complementary Nucleotide Sequence: a sequence of nucleotides in a single-stranded molecule of DNA or RNA that is sufficiently complementary to that on another single strand to specifically (non-randomly) hybridize to it with consequent hydrogen bonding.

Conserved: a nucleotide sequence is conserved with respect to a preselected (reference) sequence if it non-randomly hybridizes to an exact complement of the preselected sequence.

Hybridization: the pairing of complementary nucleotide sequences (strands of nucleic acid) to form a duplex, heteroduplex or complex containing more than two single-stranded nucleic acids by the establishment of hydrogen bonds between/among complementary base pairs. It is a specific, i.e. non-random, interaction between/among complementary polynucleotides that can be competitively inhibited. Hybridization product: The product formed when a polynucleotide hybridizes to a single or double-stranded nucleic acid. When a polynucleotide hybridizes to a double-stranded nucleic acid, the hybridization product formed is referred to as a triple helix or triple-stranded nucleic acid molecule. Moser et al, *Science*, 238:645–50 (1987).

Nucleotide Analog: a purine or pyrimidine nucleotide that differs structurally from an A, T, G, C, or U, but is sufficiently similar to substitute for the normal nucleotide in a nucleic acid molecule. Inosine (I) is a nucleotide that can hydrogen bond with any of the other nucleotides, A, T, G, C, or U. In addition, methylated bases are known that can participate in nucleic acid hybridization.

B. Methods

The present invention broadly contemplates an improvement to well known nucleic acid hybridization methods. The improvement comprises the use of SSB in the hybridization reaction admixtures to decrease the amount of nonspecific hybridization between complementary nucleic acids.

Because of the basic nature of the hybridization reaction in recombinant nucleic acid technologies, it is contemplated that the improvement can be practiced on other methods not specifically described herein that utilize hybridization as a part of the method. Therefore the following discussion is not intended to limit the present invention, but is provided to illustrate the application of principles that can be relied on to improve nucleic acid hybridization methods in general.

1. Single-stranded Nucleic Acid Binding Protein

In all embodiments described herein there is a single-stranded nucleic acid binding protein (SSB) included in the hybridization reaction admixture.

"Single-stranded nucleic acid binding protein" as used herein refers to a class of proteins collectively referred to by the term SSB. Chase et al, *Ann. Rev. Biochem.*, 55:103–36 (1986). (The art cited herein is hereby incorporated by reference.) SSB has the general property of preferential binding to single-stranded (ss) over double-stranded (ds) nucleic acids irrespective of the nucleotide sequence. The class includes such diverse members as Eco SSB, T4 gp32, T7 SSB, N4 SSB, Ad SSB, UP1, and the like. Chase et al, *Ann. Rev. Biochem.*, 55:103–36 (1986); and Coleman et al, *CRC Critical Reviews in Biochemistry*, 7(3):247–289 (1980).

SSB has a strong binding affinity for ssRNA almost as well as ssDNA, and binds dsDNA substantially less well. For example, Eco SSB in general binds ssDNA ten times better than ssRNA, and $10^3$ times better than dsDNA. Chase et al, *Ann. Rev. Biochem*; 55:103–36 (1986).

A preferred SSB for use in the methods disclosed herein is Eco SSB or T4 gp32. More preferred and exemplary of the disclosed methods is Eco SSB, whose preparation and use is described herein.

SSB has other general properties described by Chase et al, *Ann. Rev. Biochem.*, 55:103–36 (1986). These properties include the ability of an SSB to reduce the melting temperature of dsDNA, to increase processivity of an accessory DNA polymerase, to bind ssDNA stoichiometrically in an amount that depends on the particular SSB protein, and to destablize secondary structures in ssDNA.

The known SSBs all exhibit the characteristic of increasing the processivity of their accessory DNA polymerases. An SSB is deemed accessory to a DNA polymerase when both the SSB and the DNA polymerase are present in the same organism and characterized as having a capacity to stimulate a particular DNA polymerase. For example, Eco SSB is accessory to *E. coli.* DNA polymerase II and III because it stimulates that polymerase's activity, but does not stimulate T4 DNA polymerase.

Other SSBs useful in practicing the present invention are modified in amino acid residue sequence in some degree as to retain the general properties as described above. For example the protein produced by the mutant allele ssb-113 in *E. coli.* produces an SSB that binds to ssDNA as well as wild-type Eco SSB but exhibits a greater capacity to lower the melting temperature of dsDNA. Chase et al, *J. Biol. Chem.*, 259:805–14 (1984). Therefore "modified" SSBs, derived by isolation of mutants or by manipulation of cloned SSB protein-encoding genes, are also contemplated for use in the presently disclosed methods.

An SSB as disclosed herein can be used alone or in combination with other SSBs in the disclosed methods.

An effective amount of one or more SSBs for use in the disclosed methods depends on the amount of nucleic acid present in the admixtures, as it is known that SSB binds to nucleic acids stoichiometrically. For example, Eco SSB binds ssDNA to a maximum of about one SSB binding site per 33 to 65 base nucleotides, depending upon the salt concentration. Lohman et al, *J. Biol. Chem.*, 260:3594–603 (1985). Therefore, an effective amount of SSB is typically in the range of 1 ng to 10 ug of SSB protein per 100 ng of nucleic acid, preferably about 0.1 ug to 5 ug, and more preferably about 0.25 ug to 2 ug of SSB protein per 100 ng nucleic acid.

To be effective in the presently contemplated methods, SSB must be admixed with a nucleic acid in the presence of an activating (effective) amount of divalent cations. Preferred divalent cations for activating SSB are $Mg^{++}$, $Mn^{++}$, $Ca^{++}$ and $Zn^{++}$. More preferably, $Mg^{++}$ is used to activate SSB. An activating amount of divalent cations is in the range of 100 uM to 30 mM, and preferably 500 uM to 20 mM, more preferably about 15 mM for hybridization reactions. Christiansen et al, *J. Mol. Biol.*, 115:441–54 (1977). When SSB is used in a PCR-based method it is preferred that the divalent cations be present in the range of 1 to 5 mM, and more preferably the divalent cation is $Mg^{++}$ used at about 1.5 mM.

SSBs can be isolated from their source organisms by standard biochemical methods involving cell lysis and protein chromatography. Particularly preferred are the methods described in Example 1 including ammonium sulfate and polyethylenimine fractionation, affinity chromatography on ssDNA-cellulose and phosphocellulose chromatography. Alternatively, several of the SSBs are commercially available.

Eco SSB can be obtained commercially from Pharmacia, Inc. (Piscataway, NJ), or can be prepared from a variety of *E.coli* strains, such as is described by Chase et al, *Nuc. Acid Res.*, 8:3215–27 (1980), or by Weiner et al, *J. Biol. Chem.*, 250:1972–80 (1975), or can purified by the method disclosed in Example 1 using any of a variety of *E. coli* strains, including *E. coli* B or *E. coli* strain K12-H1-TRP containing the plasmid pTL119A-5.

T4 gp32 can be obtained commercially from Pharmacia, Bio-Rad (Richmond, Calif.) or Boeringer Mannheim Biochemicals (Indianapolis, Ind.), or can be prepared from a T4 infected bacterial culture such as is described by Jarvis et al, *J. Biol. Chem.*, 264:12709–16 (1989).

Because SSB is utilized in the methods of this invention in admixture with nucleic acids, it is preferred that SSB be substantially free of nuclease activity. By "substantially free of nuclease activity" is meant that on admixture and incubation of an SSB preparation with target nucleic acid molecules under hybridization reaction conditions, more than 70 percent of the target nucleic acid molecules, and preferably more than 95 percent of the target molecules, retain the capacity to hybridize with complementary polynucleotide molecules when measured by a hybridization procedure such as is described in Example 2. SSB substantially free of nuclease activity (isolated SSB) can be prepared by the methods described in Example 1, or can be obtained from the commercial vendors described above.

Where SSB is to be utilized in a hybridization method in which a hybridization reaction admixture containing SSB is subjected to a temperature in the range of about 30 degrees centigrade (30° C.) to about 100° C., it is preferred that the SSB is a heat-stable SSB. A "heat-stable SSB" as defined herein is an SSB that retains more than 90% of its pretreatment capacity to bind ssDNA preferentially over dsDNA irrespective of the nucleotide sequence of the ssDNA after exposure in a hybridization reaction admixture to 90 degrees C. (90° C.) for 10 min, preferably after exposure to 95° C. for 10 min, and more preferably after exposure to 100° C. for 8 min. A preferred heat-stable SSB is Eco SSB, that retains about 90% of its capacity to bind ssDNA after exposure to 100° C. for 8 min. Weiner et al, *J. Biol. Chem.*, 250:1972–80 (1975).

2. Preparation of Polynucleotides

The term "polynucleotide" as used herein refers to a nucleic acid molecule comprised of a linear strand of two or more deoxyribonucleotides and/or ribonucleotides, preferable more than 3. The exact size will depend on many factors, which in turn depends on the ultimate conditions of use, as is well known in the art. Polynucleotides used in the present invention include primers, probes, and the like.

The term "primer" as used herein refers to a polynucleotide, whether purified from a nucleic acid restriction digest or produced synthetically, which is capable of acting as a point of initiation of synthesis when placed under conditions in which synthesis of a primer extension product which is complementary to a template nucleic acid strand is induced, i.e., in the presence of nucleotides and an agent for polymerization such as DNA polymerase, reverse transcriptase and the like, and at a suitable temperature and pH.

The primer must be sufficiently long to prime the synthesis of extension products in the presence of the agents for polymerization. The exact lengths of the primers will depend on many factors, including temperature and the source of primer. For example, depending on the complexity of the template sequence, a polynucleotide primer typically contains 15 to 25 or more nucleotides, although it can contain fewer nucleotides. As few as 8 nucleotides in a polynucleotide primer have been reported as effective for use. Studier et al, *Proc. Natl. Acad. Sci. USA*, 86:6917–21 (1989). Short primer molecules generally require lower temperatures to form sufficiently stable hybridization complexes with template to initiate primer extension.

The primers used herein are selected to be "substantially" complementary to the different strands of each specific sequence to be synthesized or amplified. This means that the primer must contain at its 3' terminus a nucleotide sequence sufficiently complementary to nonrandomly hybridize with its respective template strand. Therefore, the primer sequence may not reflect the exact sequence of the template. For example, a non-complementary polynucleotide can be attached to the 5' end of the primer, with the remainder of the primer sequence being substantially complementary to the strand. Such noncomplementary polynucleotides might code for an endonuclease restriction site or a site for protein binding. Alternatively, noncomplementarity bases or longer sequences can be interspersed into the primer, provided the primer sequence has sufficient complementarity with the sequence of the strand to be synthesized or amplified to non-randomly hybridize therewith and thereby form an extension product under polynucleotide synthesizing conditions.

Sommer et al, *Nuc. Acid Res.*, 17:6749 (1989), reports that primers having as little as a 3 nucleotide exact match at the 3' end of the primer were capable of specifically initiating primer extension products, although less nonspecific hybridization occurs when the primer contains more nucleotides at the 3' end having exact complementarity with the template sequence. Therefore, a substantially complementary primer as used herein must contain at its 3' end at least 3 nucleotides having exact complementarity to the template sequence. A substantially complementary primer preferably contains at least 10 nucleotides, more preferably at least 18 nucleotides, and still more preferably at least 24 nucleotides, at its 3' end having the aforementioned complementarity. Still more preferred are primers whose entire nucleotide sequence have exact complementarity with the template sequence.

The choice of a primer's nucleotide sequence depends on factors such as the distance on the nucleic acid from the region coding for the desired specific nucleic acid sequence present in a nucleic acid of interest and its hybridization site on the nucleic acid relative to any second primer to be used.

The primer is preferably provided in single-stranded form for maximum efficiency, but may alternatively be double stranded. If double stranded, the primer is first treated to separate its strands before being used to prepare extension products. Preferably, the primer is a polydeoxyribonucleotide.

Polynucleotides can be prepared by a variety of methods including de novo chemical synthesis of polynucleotides and derivation of nucleic acid fragments from native nucleic acid sequences existing as genes, or parts of genes, in a genome, plasmid, or other vector, such as by restriction endonuclease digest of larger double-stranded nucleic acids and strand separation or by enzymatic synthesis using a nucleic acid template.

De novo chemical synthesis of a polynucleotide can be conducted using any suitable method, such as, for example, the phosphotriester or phosphodiester methods. See Narang et al, *Meth. Enzymol.*, 68:90, (1979); U.S. Pat. No. 4,356,270; Itakura et al, *Ann. Rev. Biochem.*, 53:323–56 (1989); and Brown et al, *Meth. Enzymol.*, 68:109, (1979).

Derivation of a polynucleotide from nucleic acids involves the cloning of a nucleic acid into an appropriate host by means of a cloning vector, replication of the vector and therefore multiplication of the amount of the cloned nucleic acid, and then the isolation of subfragments of the cloned nucleic acids. For a description of subcloning nucleic acid fragments, see Maniatis et al, *Molecular Cloning: A Laboratory Manual*, Cold Spring Harbor Laboratory, pp 390–401 (1982); and see U.S. Pat. No. 4,416,988 and No. 4,403,036.

3. Preparing Primed Template

In one embodiment, the present invention contemplates an improved method for hybridizing a primer to a template sequence present on a nucleic acid to form a primer-template hybridization product (primed template). A hybridization reaction admixture is prepared by admixing effective amounts of a primer, a template nucleic acid and other components compatible with a hybridization reaction including an effective amount of a single-stranded nucleic acid binding protein (SSB).

The primary purpose in including SSB in the hybridization reaction admixture is to reduce nonspecific hybridization reactions. Because nonspecific hybridization occurs more frequently as the complexity of the template nucleic acid increases, the benefits of including SSB in primer-template hybridization reaction admixtures increase as the complexity of the template increases. Thus, the method of the present invention is particularly useful where the template nucleic acid has a complexity comparable to that of lambda bacteriophage DNA. The benefits are even more pronounced where the complexity of template is comparable to a procaryotic or eucaryotic genome.

Template nucleic acid sequences to be hybridized in the present methods can be present in any nucleic acid-containing sample so long as the sample is in a form, with respect to purity and concentration, compatible with nucleic acid hybridization reaction. Isolation of nucleic acids to a degree suitable for hybridization is generally known and can be accomplished by a variety of means. For instance, nucleic acids can be isolated from a variety of nucleic acid-containing samples including body tissue, such as skin, muscle, hair, and the like, and body fluids such as blood, plasma, urine, amniotic fluids, cerebral spinal fluids, and the like. See, for example, Maniatis et al, *Molecular Cloning: A Laboratory Manual*, Cold Spring Harbor Laboratory (1982); and Ausubel et al, *Current Protocols in Molecules Biology*, John Wiley and Sons (1987).

The hybridization reaction mixture is maintained under hybridizing conditions for a time period sufficient for the primer to hybridize to complementary nucleic acid sequences present in the sample to form a hybridization product, i.e., a complex containing primer and template nucleic acid strands.

The phrase "hybridizing conditions" and its grammatical equivalents, when used with a maintenance time period, indicates subjecting the hybridization reaction admixture, in the context of the concentrations of reactants and accompanying reagents in the admixture, to time, temperature and pH conditions sufficient to allow the primer to anneal with the template sequence, typically to form a nucleic acid duplex. Such time, temperature and pH conditions required to accomplish hybridization depend, as is well known in the art, on the length of the primer to be hybridized, the degree of complementarity between the primer and the template, the guanidine and cytosine content of the polynucleotide, the stringency of hybridization desired, and the presence of salts or additional reagents in the hybridization reaction admixture as may affect the kinetics of hybridization. Methods for optimizing hybridization conditions for a given hybridization reaction admixture are well known in the art.

Typical hybridizing conditions include the use of solutions buffered to pH values between 4 and 9, and are carried out at temperatures from 18 degrees C. (18° C) to 75° C., preferably about 37° C. to about 65° C., more preferably about 54° C., and for time periods from 0.5 seconds to 24 hours, preferably 2 min.

Hybridization can be carried out in a homogeneous or heterogeneous format as is well known. The homogeneous hybridization reaction occurs entirely in solution, in which both the primer and template sequences to be hybridized are present in soluble forms in solution. A heterogeneous reaction involves the use of a matrix that is insoluble in the reaction medium to which either the primer or template is bound.

Also preferred are the homogeneous hybridization reactions such as are conducted for a reverse transcription of isolated mRNA to form cDNA, dideoxy sequencing and other procedures using primer extension reactions in which primer hybridization is a first step. Particularly preferred is the homogeneous hybridization reaction in which the template is amplified via a polymerase chain reaction (PCR).

The use of a SSB in a hybridization reaction admixture reduces the degree of nonspecific hybridization of a primer to a template nucleic acid. Therefore hybridization conditions can be carried out at temperatures lower than normally required to maintain high stringency, i.e., high specificity, in the hybridization reaction.

Where the nucleic acid containing a template sequence is in a double-stranded (ds) form, it is preferred to first denature the dsDNA, as by heating or alkali treatment, prior to conducting the hybridization reaction. The denaturation of the dsDNA can be carried out prior to admixture with a primer to be hybridized, or it can be carried out after the admixture of the dsDNA with the primer, the SSB or both. Where the primer itself is provided as a double-stranded molecule, it too can be denatured prior to admixture, or it can be denatured concurrently with the template-containing dsDNA.

4. Primer Extension Reactions

The primed template can be used to produce a strand of nucleic acid having a nucleotide sequence complementary to the template, i.e., a template-complement.

If the template whose complement is to be produced is in the form of double stranded nucleic acid, it is typically first denatured, usually by melting, into single strands, such as ssDNA. The nucleic acid is then subjected to a (first) primer extension reaction by treating (contacting) the nucleic acid with a (first) polynucleotide synthesis primer having as a portion of its nucleotide sequence a sequence selected to be substantially complementary to a portion of the sequence of the template. The primer is capable of initiating a primer extension reaction by hybridizing to a specific nucleotide sequence, preferably at least about 8 nucleotides in length and more preferably at least about 20 nucleotides in length. This is accomplished by mixing an effective amount of the primer with the template nucleic acid, an effective amount of SSB, and an effective amount of nucleic acid synthesis inducing agent to form a primer extension reaction admixture. The admixture is maintained under polynucleotide synthesizing conditions for a time period, which is typically predetermined, sufficient for the formation of a primer extension reaction product.

The primer extension reaction is performed using any suitable method. Generally polynucleotide synthesizing conditions are those wherein the reaction occurs in a buffered aqueous solution, preferably at a pH of 7–9, most preferably about 8. Preferably, a molar excess (for genomic nucleic acid, usually about $10^6:1$ primer:template) of the primer is admixed to the buffer containing the template strand. A large molar excess is preferred to improve the efficiency of the process. For polynucleotide primers of about 20 to 25 nucleotides in length, a typical ratio is in the range of 50 ng to 1 ug, preferably 250 ng, of primer per 100 ng to 500 ng of mammalian genomic DNA or per 10 to 50 ng of plasmid DNA.

The deoxyribonucleotide triphosphates (dNTPs) dATP, dCTP, dGTP, and dTTP are also admixed to the primer extension reaction admixture in amounts adequate to support the synthesis of primer extension products, and depends on the size and number of products to be synthesized. The resulting solution is heated to about 90° C.–100° C. for about 1 to 10 minutes, preferably from 1 to 4 minutes. After this heating period the solution is allowed to cool to room temperature, which is preferable for primer hybridization. To the cooled mixture is added an appropriate agent for inducing or catalyzing the primer extension reaction, and the reaction is allowed to occur under conditions known in the art. The synthesis reaction may occur at from room temperature up to a temperature above which the inducing agent no longer functions efficiently. Thus, for example, if DNA polymerase is used as inducing agent, the temperature is generally no greater than about 40° C. unless the polymerase is heat-stable.

The inducing agent may be any compound or system which will function to accomplish the synthesis of primer extension products, including enzymes. Suitable enzymes for this purpose include, for example, *E. coli*, DNA polymerase I, Klenow fragment of *E. coli* DNA polymerase I, T4 DNA polymerase, T7 DNA polymerase, recombinant modified T7 DNA polymerase, other available DNA polymerases, reverse transcriptase, and other enzymes, including heat-stable enzymes, which will facilitate combination of the nucleotides in the proper manner to form the primer extension products which are complementary to each nucleic acid strand.

Heat-stable DNA polymerases are particularly preferred as they are stable in a most preferred embodiment in which PCR is conducted in a single solution in which the temperature is cycled. Representative heat-stable polymerases are the DNA polymerases isolated from *Bacillus stearothermophilus* (Bio-Rad), *Thermus thermophilus* (FINZYME, ATCC #27634), Thermus species (ATCC #31674), *Thermus aquaticus* strain TV 1151B (ATCC #25105), *Sulfolobus acidocaldarius*, described by Bukhrashuili et al, *Biochem. Biophys. Acta*, 1008:102–7 (1989) and by Elie et al, *Biochem. Biophys. Actz*, 951:261–7 (1988), and *Thermus filiformis* (ATCC #43280). Particularly preferred is Taq DNA polymerase available from a variety of sources including Perkin Elmer Cetus, (Norwalk, Conn.), Promega (Madison, Wis.) and Stratagene (La Jolla, Calif.), and AmpliTaq™ DNA polymerase, a recombinant Taq DNA polymerase available from Perkin-Elmer Cetus.

Generally, the synthesis will be initiated at the 3' end of each primer and proceed in the 5' direction along the template strand, until synthesis terminates, producing molecules of different lengths. There may be inducing agents, however, which initiate synthesis at the 5' end and proceed in the above direction, using the same process as described above.

The primer extension reaction product can then be subjected to a second primer extension reaction by treating it with a second polynucleotide synthesis primer having a preselected nucleotide sequence. The second primer is capable of initiating the second reaction by hybridizing to a nucleotide sequence, preferably at least about 8 nucleotides in length and more preferably at least about 20 nucleotides in length, found in the first product. This is accomplished by mixing the second primer, preferably a predetermined amount thereof, with the first product, preferably a predetermined amount thereof, to form a second primer extension reaction admixture. The admixture is maintained under polynucleotide synthesizing conditions for a time period, which is typically predetermined, sufficient for the formation of a second primer extension reaction product.

In preferred strategies, the first and second primer extension reactions are the first and second primer extension reactions in a polymerase chain reaction (PCR).

PCR is carried out by simultaneously cycling, i.e., performing in one admixture, the above described first and second primer extension reactions, each cycle comprising polynucleotide synthesis followed by denaturation of the double stranded polynucleotides formed. Methods and systems for amplifying a specific nucleic acid sequence are described in U.S. Pat. No. 4,683,195 and No. 4,683,202, both to Mullis et al; and the teachings in *PCR Technology*, Erlich, ed., Stockton Press (1989); Faloona et al, *Methods in Enzymol.*, 155:335–50 (1987); and *Polymerase Chain Reaction*, Erlich et al., eds., Cold Spring Harbor Laboratories Press (1989).

In one embodiment, a method of amplifying a specific double-stranded nucleic acid sequence in a nucleic acid sample is contemplated. The method comprises the steps of:

(a) Separating the strands of the double-stranded nucleic acid molecule to form single-stranded templates.

(b) Treating the single-stranded templates with the following in amounts effective to induce polynucleotide synthesis under polynucleotide synthesizing conditions: (i) primers that are selected so as to be substantially complementary to portions of the different strands of the specific double-stranded sequence to hybridize therewith such that an extension product synthesized from one primer, when it is separated from its template (complementary) nucleic acid strand, can serve as a template for synthesis of the extension product of the other primer, (ii) an SSB, preferably Eco SSB, and (iii) an enzyme capable of producing primer extension products from said single-stranded templates, wherein said treatment is conducted under conditions such that the primers hybridize to the specific sequences and an extension product of each primer is synthesized by the action of the enzyme, said product being complementary to each single-stranded template.

(c) Separating the primer extension products formed in step (b) from the templates on which they are synthesized to produce single-stranded molecules.

(d) Treating the single-stranded molecules produced in step (c) with effective amounts of the primers, SSB and enzyme of step (b) under conditions such that a primer extension product is synthesized using the single-stranded molecules formed in step (c) as a template.

PCR is carried out by cycling i.e., simultaneously performing in one admixture, the above described: 1) denaturing step to form single-stranded templates, 2) hybridization step to hybridize primer to ss template, and 3) primer extension steps to form the extended product. PCR is performed in the above sequence (cycle) by changing the temperature of the PCR mixture to a temperature compatible with each step, in series.

The primer extension reaction conditions involve maintaining the reaction mixture for a time period and at a temperature sufficient for a DNA polymerase primer extension reaction to occur to produce primer extension products as is well known. Conditions for conducting a primer extension reaction are well known. In a PCR format, the maintenance is carried out quickly to conveniently facilitate numerous cycles, in about 1 second to 5 minutes, preferably about 1.5 minutes, and at about 40° C. to 75° C., preferably about 72° C. Conducting at least one cycle of PCR results in the formation of amplified nucleic acid products. The PCR is typically conducted with at least 15 cycles, and preferably with about 20 to 40 cycles.

Hybridizing conditions were described earlier and are suitable for use in the PCR format. However, it is preferred and convenient to conduct hybridization in short periods of time, in 5 seconds to 12 minutes, preferably in 2 minutes, and in the temperature range of 30° C. to 75° C., preferably about 40° C. to 65° C., and more preferably about 54° C.

A suitable SSB for use in a hybridization reaction mixture is one of the class of SSBs described previously, preferably a nuclease free, heat-stable SSB, and more preferably is Eco SSB. Exemplary hybridization reaction mixtures and reaction conditions are described further in Example 2.

In preferred embodiments, detecting the presence of any primer extension product formed in step (d) thereby provides a method for detecting the presence of a specific double-stranded nucleic acid sequence in the sample.

Detection of amplified nucleic acid product can be accomplished by any of a variety of well known techniques. In a preferred embodiment, the amplified product is separated on the basis of molecular weight by gel electrophoresis, and the separated products are then visualized by the use of nucleic acid specific stains which allow one to observe the discreet species of resolved amplified product present in the gel. Although numerous nucleic acid specific stains exist and would be suitable to visualize the electrophoretically separated nucleic acids, ethidium bromide is preferred.

Alternative methods suitable to detect the amplified nucleic acid product include hybridization-based detection means that use a labeled polynucleotide probe capable of hybridizing to the amplified product. Exemplary of such detection means include the Southern blot analysis, ribonuclease protection analysis using in vitro labeled polyribonucleotide probes, and the like methods for detecting nucleic acids having specific nucleotide sequences. See, for example, Ausubel et al., *Current Protocols in Molecular Biology*, John Wiley & Sons, 1987.

In one approach for detecting the presence of a specific nucleic acid sequence, the deoxyribonucleotide triphosphates (dNTPs) used in the primer extension reaction include a label or indicating group that will render a primer extension product detectable. Typically such labels include radioactive atoms, chemically modified nucleotide bases, and the like.

Radioactive elements operatively linked to or present as part of a dNTP provide a useful means to facilitate the detection of a DNA primer extension product. A typical radioactive element is one that produces beta ray emissions. Elements that emit beta rays, such as $^3$H, $^{14}$C, $^{32}$P, and $^{35}$S represent a class of beta ray emission-producing radioactive element labels.

Alternatives to radioactively labeled dNTPs are dNTPs that are chemically modified to contain metal complexing agents, biotin-containing groups, fluorescent compounds, and the like.

One useful metal complexing agent is a lanthanide chelate formed by a lanthanide and an aromatic beta-diketone, the lanthanide being bound to the nucleic acid or polynucleotide via a chelate forming compound such as an EDTA-analogue so that a fluorescent lanthanide complex is formed. See U.S. Pat. No. 4,374,120, and No. 4,569,790 and published International Pat. Applications No. EP0139675 and No. WO87/02708.

Biotin or acridine ester-labeled oligonucleotides and their use in polynucleotides have been described. See U.S. Pat. No. 4,707,404, published International Pat. Application EP0212951 and European Patent No. 0087636. Useful fluorescent marker compounds include fluorescein, rhodamine, Texas Red, NBD and the like.

A labeled nucleotide residue present in a nucleic acid renders the nucleic acid itself labeled and therefore distinguishable over other nucleic acids present in a sample to be assayed. Detecting the presence of the label in the nucleic acid and thereby the presence of the specific nucleic acid sequence, typically involves separating the nucleic acid from any labeled dNTP that is not present as part of a primer extension reaction product.

Numerous applications of the PCR-based amplification method are contemplated that will be readily apparent to one skilled in the art. For example, cloning mRNA through reverse transcription to produce cDNA can be made more sensitive by the use of PCR-based amplification of the produced cDNA. Insofar as nucleic acid sequencing can be conducted on PCR-amplified nucleic acid, the present invention can be used to improve the amplified nucleic acids production step in a sequencing procedure. A variety of the other recombinant DNA cloning and nucleic acid manipulative steps have been described that involved PCR. See, for example, *PCR Technology*, Erlich, ed., Stockton Press (1989), and *Polymerase Chain Technology*, Erlich et al, eds., Cold Spring Harbor Laboratory Press (1989).

In a related embodiment, the present invention contemplates the application of the improved PCR amplification method to samples of nucleic acid in which the nucleic acid is hybridized and primer extension products are formed from a hybridization product comprised of triple-stranded nucleic acid molecules. Triple-stranded nucleic acid molecules, or triple helixes, have been produced in vitro by hybridization of polynucleotides and duplex DNA. Moser et al, *Science*, 238:645–50 (1987); Kohwi et al, *Proc. Natl. Acad. Sci. USA*, 85:3781–85 (1988); Wells et al, *FASEB J.*, 2:2939–49 (1988); Htun et al, *Science*, 243:1571–76 (1989); and Rajagopal et al, *Nature*, 339:637–40 (1989). Therefore although a preferred template for hybridization and primer extension in a PCR method is a single-stranded nucleic acid, the invention contemplates the use of a double-stranded template to form a triple-stranded hybridization product.

In practicing the methods of the present invention to form a triple-stranded hybridization product, it is to be understood that the initial denaturation of double-stranded nucleic acids to form single-stranded template is not required. Instead, the hybridization reaction mixture can be used to treat double-stranded template rather than single-stranded template forming a triple helix hybridization product.

C. Compositions

Also contemplated by the present invention is a composition for producing a template-complement from a nucleic acid template that contains a specific nucleic acid sequence according to the methods of the present invention. The composition comprises, in amounts sufficient to produce at least one template-complement, (a) an isolated single-stranded nucleic acid binding protein, and (b) a polynucleotide primer selected so as to be sufficiently complementary to a portion of a nucleic acid template containing said specific nucleic acid sequence to hybridize therewith such that a primer extension product can be synthesized therefrom in a primer extension reaction.

In another embodiment, a composition for producing a template-complement comprises effective amounts of (a) an isolated single-stranded nucleic acid binding protein, and (b) an inducing agent for nucleic acid synthesis by primer extension. A preferred inducing agent is one of the previously described DNA polymerase enzymes suitable for the synthesis of primer extension products.

In one embodiment for amplifying a specific nucleic acid via the PCR, composition comprises, in effective amounts, (a) an isolated single-stranded nucleic acid binding protein and (b) two polynucleotide primers that are selected so as to be substantially complementary to portions of different strands of a double-stranded nucleic acid containing said specific nucleic acid sequence to hybridize therewith such that an extension product synthesized from one primer, when it is separated from its complementary nucleic acid strand, can serve as a template for synthesis of the extension product of the other primer.

In all embodiments of a contemplated composition additional reagents can also be included such as a divalent cation, preferably $Mg^{++}$, $Mn^{++}$, $Ca^{++}$, or $Zn^{++}$, and preferably an amount of divalent cation sufficient to produce a primer extension reaction mixture having an effective amount of divalent cation concentration in the range of 0.5 mM to 20 mM. Where the composition is formulated for use in PCR-based methods, it is preferred that the divalent cation is $Mg^{++}$ and the effective amount is about 1.5 mM.

The single-stranded binding protein (SSB) for inclusion in a composition of this invention is one of the SSBs described herein for practicing a contemplated method. The amount of SSB to be included in a system is an amount sufficient to produce a reaction mixture having an effective amount of SSB in the range of 1 ng to 10 ng per 100 ng of nucleic acid, and more preferably is about 0.25 ug to 2 ug of SSB per 100 ng of nucleic acid.

A particularly preferred composition for use in PCR includes isolated Eco SSB, $Mg^{++}$ in an amount sufficient to produce a reaction mixture concentration of about 1.5 mM, and a heat-stable DNA polymerase, preferably Taq polymerase. An additional reagent for this embodiment can be two polynucleotide primers selected having the capacity to function in PCR as described above.

The compositions can be packaged in kit form. As used herein, the term "package" refers to a solid matrix or material customarily utilized in a system and capable of holding within fixed limits one or more of the reagent components for use in a method of the present invention. Such materials include glass and plastic (e.g., polyethylene, polypropylene and polycarbonate) bottles, vials, paper, plastic and plastic-foil laminated envelopes and the like. Thus, for example, a package can be a glass vial used to contain the appropriate quantities of polynucleotide primer(s), isolated SSB, a divalent cation and a DNA polymerase, or a combination thereof.

In embodiments where the system is utilized diagnostically to detect the presence of a specific nucleic acid, it is preferred that the diagnostic system further includes a label or indicating means capable of signaling the formation of a complex containing a polynucleotide by the methods of the present invention.

In preferred embodiments, the indicating means comprises a probe, the probe being operatively linked to a label, thereby providing a means to detect an amplified nucleic acid product formed. Preferred labels are those discussed hereinbefore, especially $^{32}P$ and $^{35}S$ for polynucleotide probes.

Kits useful for producing a template-complement or for amplification or detection of a specific nucleic acid sequence using a primer extension reaction methodology also typically include, in separate containers within the kit, dNTPs where N is adenine, thymine, guanine and cytosine, and other like agents for performing primer extension reactions.

The reagent species, indicating means or primer extension reaction reagents of any system described herein can be provided in solution, as a liquid dispersion or as a substantially dry power, e.g., in lyophilized form. Where the reagent species or indicating means is an enzyme, the enzyme's substrate can also be provided in a separate package of a system. A solid support and one or more buffers can also be included as separately packaged elements in this system.

EXAMPLES

The following examples are given for illustrative purposes only and do not in any way limit the scope of the invention.

1. Purification of Single-Stranded Nucleic Acid Binding Protein

Single-stranded nucleic acid binding protein (Eco SSB) was purified from *E. coli* strain K12-H1-TRP/pTL119A-5 essentially as previously described by Lohman et al., *Biochem.*, 25:21–25 (1986), according to the following procedure.

a. Cell Growth and Induction

*E. coli* strain K12-H1-TRP/pTL119A-5 was grown at 30 degrees centigrade (30° C.) in media containing 10 grams per liter (g/l) bactotryptone, 5 g/l yeast extract, 5 g/l NaCl and 2 ml/l of a solution containing 50 mg/ml thiamine. Single colony isolates of SSB-coli were admixed with 100 mls of media and grown overnight at 30° C. to produce an overnight culture. 5 ml of the overnight culture was admixed per 1 liter of media in a 2 liter flask and the admixture maintained at 30° C. until the bacterial cells had grown to an optical density at 600 nanometers (O.D. 600) of 0.4 to 0.6 to produce a log-phase culture. 18 liters of log-phase culture were produced by this procedure.

The log-phase culture was then heat shocked by maintaining the culture at 42° C. for thirty minutes. The heat shocked culture was maintained for four to five hours at 37° C. Thereafter culture was placed on ice and the bacterial cells collected from the culture by centrifugation at 5,000 rpm in a J-6B rotor (Beckman Instruments, Palo Alto, Calif.) for ten minutes at 4° C. All buffers and procedures utilized hereafter were at 4° C. unless otherwise noted. The resulting bacterial cell pellet was resuspended in a 0.5 liter solution containing 10 mM Tris-HCl at pH 8.0, 1 mM ethylenediaminetetraacetic acid (EDTA) and 0.1M NaCl. The resuspended pellet was centrifuged for ten minutes at 5,000 rpm in the same rotor at 4° C., and the resulting cell pellet was resuspended in 500 ml of a lysis solution containing 50 mM Tris-HCl at pH 8.3, 0.2M NaCl, 15 mM spermidine trichloride, 1 mM EDTA and 10% sucrose. The resulting cell pellet suspension was frozen by addition drop by drop to liquid nitrogen and stored at −70° C. until used.

b. Cell Lysis

The frozen bacterial cells were thawed overnight to 0° C. in a freezer. The cells were then thawed in a warm water bath with gentle mixing at slightly below 10° C. Freshly prepared 0.1M phenylmethylsulfonyl fluoride (PMSF) was added to a final concentration of 0.1 mM. A solution containing 10 mg/ml of lysozyme was added to the solution to a final concentration of 200 ug/ml. The resulting solution was maintained at 4° C. for thirty minutes. A freshly prepared solution of 4% sodium deoxycholate in H20 was admixed to the solution to a final concentration of 0.05%. The resulting solution was maintained at 15° C. for thirty minutes to lyse the bacterial cells and produce a lysate. This lysate was sonicated for three minutes at 50% duty cycle on a power setting of 10 using a model 250 sonicator manufactured by Branson (Danbury, Conn.). The lysate was then centrifuged in a SA 600 rotor (Sorval, Dupont, Wilmington, Del.) at 14,000 rpm for sixty minutes at 4° C. The resulting supernatant was collected and termed fraction I.

c. Purification of Cell Lysate

A solution containing 10% Polymin P (PEI; polyethylenimine) at pH 6.9 (Sigma Chemical Corp., St. Louis, Mo.) was slowly admixed with 250 ml of fraction I to a final concentration of 0.4%. The resulting solution was stirred gently for fifteen minutes to precipitate protein. The precipitate was collected by centrifugation in 60 ml capped tubes in a SA 600 rotor at 14,000 rpm for twenty minutes at 4° C. The resulting pellet was gently resuspended in 250 ml of a solution containing 50 mM Tris-HCl at pH 8.3, 1 mM EDTA, 0.4M NaCl and 20% glycerol by first gently breaking the pellets with a tissue homogenizer and then slowly stirring the solution at 4° C. for thirty minutes. After the pellet appears to be completely resuspended, the solution is stirred for an additional fifteen minutes at 4° C. The insoluble debris is then removed by centrifugation at 14,000 rpm in a SA 600 rotor for twenty minutes at 4° C. The resulting supernatant is collected and termed fraction II.

Solid ammonium sulfate was slowly added over a thirty minute period to fraction II with constant stirring at 4° C. until approximately 27% saturation with ammonium sulfate was reached. This solution was stirred for an additional thirty minutes at 4° C. and then centrifuged for thirty minutes in 60 ml capped tubes at 14,000 rpm in a SA 600 rotor at 4° C. The resulting pellets were gently resuspended in 225 ml of a solution containing 50 mM Tris-HCl at pH 8.3, 1 mM EDTA, 0.3M NaCl and 20% glycerol. After the pellet is completely resuspended the solution is centrifuged at 14,000 rpm for twenty minutes at 4° C. in a SA 600 rotor to remove any insoluble material. The resulting supernatant is termed fraction III.

Fraction III containing approximately 225 mg protein in 225 ml was dialyzed against 4 liters of dialysis solution containing 50 mM Tris HCl at pH 8.3, 1 mM EDTA, 150 mM NaCl and 20% glycerol for 12 to 18 hours. A portion of the dialyzed fraction III containing about 50 mg protein was diluted in the dialysis solution until its conductivity was brought to within 10% of the conductivity of dialysis solution, and was then applied to a 5.0×10.0 cm P-11 phosphocellulose column (Whatman Inc., Clifton, N.J.) that had been previously activated according to the manufacturer's instructions and equilibrated with dialysis solution. The dialyzed and diluted fraction III was loaded onto the P-11 phosphocellulose column at a flow rate of 6 ml/minute. The phosphocellulose column was washed with 400 ml of column buffer containing 50 mM Tris-HCl at ph 8.3, 1 mM EDTA, 150 mM NaCl and 20% glycerol to remove any proteins that did not bind to the phosphocellulose column. Proteins that bound the P-11 phosphocellulose column were eluted with a linear gradient of KCl ranging from a concentration of 0M to 2.0M in column buffer. Fractions containing 10 ml of eluate were collected and the optical density at 280 nm measured. Peak fractions were pooled and dialyzed against a 4 liter solution containing 20 mM Tris-HCl , pH 8.3, 1 mM EDTA, 500 mM NaCl, 1 mM beta-mercaptoethanol and 50% glycerol and stored at −20° C. until used. The resulting solution contained Eco SSB protein at a concentration of 1 mg per ml and was free of nuclease contamination.

2. Detection of Specific Nucleic Acid Sequences in Genomic DNA Using the Polymerase Chain Reaction Genomic DNA was purified by phenol extraction and alcohol precipitation according to the procedures of Ausubel et al, *Current Protocols in Molecular Biology*, John Wiley and Sons (1987), from blood obtained by tail bleed from a transgenic mouse having about 1 to 2 copies of a lambda transgene vector, and is referred to as lambda transgene mouse genomic DNA. Genomic DNA was also obtained from human white blood cells by the procedure of Miller et al, *Nuc. Acid Res.*, 16:1215 (1988), and referred to as human genomic DNA.

Polynucleotide primers having the deoxyribonucleotide sequences shown in Table 1 below were prepared by chemical synthesis using a model 381A polynucleotide synthesizer (Applied Biosystems, Inc., Foster City, Calif.) according to the manufacturer's instructions.

TABLE 1

| Poly-nucleo-tide Designation | Nucleotide Base Sequence |
| --- | --- |
| pr 886 | 5'-TCTGGCTCCAGCCAAAGCCACCCTAG-3' |
| pr 887 | 5'-GGCTGAGCCCAGTGCCTCTTGAGTA-3' |
| pr 4266 | 5'-GGTGCGACGACTCCTGGAGCCC-3' |
| pr 19102 | 5'-GACAGTCACTCCGGCCCGTGCGG-3' |
| pr 1A | 5'-TGTAAAACGACGGCCAGTGGGGCGGCC ACAATTTCGCGCCAAACTTGACCG-3' |
| pr 1B | 5'-CAGGAAACAGCTATGACCGTGGGCAGC CTGCGCCCGTTTGGGTCC-3' |
| pr 2A | 5'-TGTAAAACGACGGCCAGTCAAGGGATA ATGTTTCGAACGCTGTTT-3' |
| pr 2B | 5'-CAGGAAACAGCTATGACCCCCAGATTA ACACGGAAAACTTTCCATTTA-3' |
| pr 737 | 5'-CGACGACTCGTGGAGCCC-3' |
| pr 738 | 5'-GACAGTCACTCCGGCCCG-3' |

A hybridization reaction admixture was formed by combining the following reagents in a sterile 0.5 milliliter (ml) microfuge tube: (a) 69 microliters (ul) of sterile, autoclaved H₂O; (b) 10 ul of 10x reaction buffer containing 500 mM KCl, 100 mM Tris-HCl (pH 8.3), 15 mM MgCl₂, and 0.1% sterile gelatin, (c) 8 ul of a solution containing 2.5 mM each of the deoxynucleotidetriphosphates (dNTP's) dGTP, dCTP, dTTP and dATP; (d) 2 ul of a solution containing 250 ng each of two polynucleotide primers, selected from Table 1 and being indicated in the legends to FIGS. 1–4, (e) 10 ul of DNA template dilution buffer (10 mM Tris-HCl, pH 8.0, 1 mM EDTA, 10 mM NaCl) containing genomic DNA as template, the particular DNA sample and amount being indicated in the legends to FIGS. 1–4; and (f) zero to 1.0 ul (as indicated) of a solution containing 1 milligram (mg) per ml of Eco SSB protein prepared in Example 1 and free of nuclease contamination.

The hybridization reaction admixture was heated to 94° C. and maintained at 94° C. for 3 min to denature the duplex DNA (genomic DNA) present and form single-stranded templates. Then the admixture was cooled to 54° C. and maintained at 54° C. for 3 min to allow hybridization to occur and form duplex DNA. The hybridized admixture was then centrifuged for 10 seconds, in a microfuge at about 12,000×g to collect condensation off the microfuge tube walls, and 0.5 ul of a solution containing 2.5 units of either Taq DNA polymerase or AmpliTaq™ DNA polymerase (Perkin-Elmer Cetus, Norwalk, Conn.) was admixed to form a primer extension reaction admixture.

Each microfuge tube containing the above-prepared primer extension reaction admixture was overlayed with 50 ul of mineral oil and then placed into a DNA Thermal Cycler (Perkin-Elmer Cetus, Norwalk, Conn.) and subjected to the following temperature and time conditions: (1) 72° C. for 1.5 min to allow for primer extension, (2) 91° C. for 1 min to heat denature the duplex DNA and (3) 54° C. for 2 min to allow single-stranded nucleic acids to hybridize. Thereafter the same tubes were subjected to further cycles of conditions (1), (2) and (3) for a total of 30 cycles according to the manufacturer's instructions. The cycled tubes were then maintained at 72° C. for 10 min, and then maintained at 4° C. for 12 hours.

The contents of each primer extension reaction admixture was then analyzed on 6% polyacrylamide gels in 1x TBE by loading 35 ul of admixture sample and 5 ul of 10x sample buffer onto an 8 centimeter gel, electrophoresing the gel at 100 v for about 1 hr, and staining the electrophoresed gel with ethidium bromide to visualize the electrophoresed nucleic acids.

The sensitivity of a PCR nucleic acid detection system using Eco SSB was determined using the above-described procedures and with the following additional details. The hybridization reaction admixture was prepared containing varying amounts of lambda transgene mouse genomic DNA, from 0.001 ng to 1000 ng. Carrier DNA comprising calf thymus DNA (100 ng) was also admixed to each tube containing less than 100 ng of genomic DNA. Duplicate sets of hybridization reaction admixtures were prepared with the varying amounts of genomic DNA; one set contained 250 ng (0.25 ul) of Eco SSB and the other set did not contain Eco SSB. The polynucleotide primers used were pr 4266 and pr 19012, whose sequences are shown in Table 1. Taq DNA polymerase was admixed in each tube and the PCR reaction mixtures were then subjected to PCR cycles as described above. The results of the sensitivity analysis are shown in FIGS. 1A and 1B.

By use of primers pr 4266 and pr 19012, an amplified nucleic acid fragment comprising a duplex DNA molecule that corresponds in sequence to the target specific nucleic acid is detected having a size of about 520 base pairs (bp), and is indicated in FIGS. 1A and 1B by the arrow. In the absence of Eco SSB (FIG. 1A), the detected duplex DNA molecule was not a significant component above the level of detection of non-specific DNA molecules until at least 100 ng of template DNA were present in the hybridization and primer extension reaction admixtures. In the presence of 250 ng of Eco SSB, the detection of nonspecific DNA molecules was substantially reduced and the limit of detection (sensitivity) for the target sequence was at least as low as 0.1 ng of template DNA (lane 3, FIG. 1B).

The amount of Eco SSB to be added to a PCR nucleic acid detection system for effective improvement of detection was also determined by the above-described procedures. The hybridization reaction admixture was prepared using from 10 ng to 10,000 ng of Eco SSB in each tube, including AmpliTaq™ DNA polymerase, 100 ng of template lambda transgene mouse genomic DNA and the primers pr 4266 and pr 19012, and the PCR cycles were conducted as before. The results of varying the Eco SSB concentration are shown in FIG. 2.

The results in FIG. 2 show that Eco SSB is effective to improve PCR-based detection of specific nucleic acids over a wide range of Eco SSB protein concentrations, from below 10 ng to above 5 ug per 100 ul of hybridization reaction admixture. Particularly desirable results were obtained in which nonspecific bands were substantially reduced at concentrations of Eco SSB above 100 ng and below 2 ug per 100 ul of hybridization reaction admixture.

The requirements for stringency in the hybridization reaction were evaluated when Eco SSB is used in a PCR-based detection system by conducting the hybridization reaction at either 42° C. or 54° C. The method was conducted as described above with the following changes. Hybridization reaction tubes were prepared containing (1) 100 ng of human genomic DNA and the primers pr 886 and pr 887, (2) 100 ng of lambda transgene mouse genomic DNA and the primers pr 4266 and pr 19012, or (3) 100 ng of the mouse DNA and the primers pr 737 and pr 738 (18-mers), and further containing either 250 ng of Eco SSB (+) or no Eco SSB (−). Duplicate sets of the above tubes were prepared, each containing Taq DNA polymerase, and were subjected to the above PCR cycles in which the hybridization (annealing) temperature was either 42° C. or 54° C. The results of the hybridization stringency determination are shown in FIG. 3.

Using the mouse genomic DNA in combination with either the primer set pr 4266 and pr 19012 (each 23-mers) (lanes 5, 6, 11 and 12) or the primer set pr 737 and pr 738 (each 18-mers) (lanes 3, 4, 9 and 10) in the PCR system with Eco SSB, a specific duplex DNA of about 520 bp is detected (FIG. 3, Lanes 4, 6, 10 and 12). Using the human genomic DNA in combination with the primer set pr 886 and pr 887 in the PCR system with Eco SSB, a specific duplex DNA of about 1800 bp is detected (lanes 7 and 8). However, in the absence of Eco SSB, the specific sequences are either not detected (lanes 1, 3, 7 and 9) or is detected in a manner in which there are significantly more nonspecific bands when compared to detection with Eco SSB (lanes 5 and 11 compared to lanes 6 and 12).

The effect of temperature on stringency of hybridization is well characterized. At lower temperatures, higher amounts of mismatched base pairs are tolerated in a hybridized duplex. The effect of lower stringency therefore is to increase the occurrence of duplex formation between single-stranded nucleic acid molecules that do not have homology or even substantial complementarity. That is, under conditions of low stringency a duplex can be formed between a primer/probe and a nucleic acid sequence that is not the target sequence desired, ie, a nonspecific hybridization product. Nonspecifically hybridized duplex DNA molecules can initiate primer extension and lead to the formation of nonspecific amplified nucleic acid molecules.

The effects of a hybridization temperature that produces conditions of lower hybridization stringency on a PCR detection system containing Eco SSB is shown in FIG. 3. As before at 54° C., Eco SSB substantially improved the signal-to-noise ratio of detection of specific nucleic acids over non-specific nucleic acids when PCR was conducted using a 42° C. hybridization temperature. Whereas reducing the hybridization temperature lowered the stringency and therefore increase the nonspecific signal (compare lanes 9 to lane 3), Eco SSB substantially reduced the amount of detectable nonspecific duplex DNA under conditions of low hybridization stringency such as 42° C. (compare lane 3 to 4, or lane 5 to 6). Therefore the use of Eco SSB in a PCR detection system or method allows for less precision in determining the critical hybridization temperature and hybridization stringency required for conducting PCR or other hybridization based methods.

The results in FIG. 3 also indicate that primers having shorter nucleotide lengths produce greater levels of nonspecific hybridization. This is not unexpected because primer length will effect the hybridization temperature (Tm). For example, compare lane 11 to lane 9, or compare lane 5 to lane 3, in which a 23 nucleotide primer exhibits more specificity than an 18 nucleotide primer. When using Eco SSB, the 18 nucleotide primer detects a specific sequence (lanes 3 and 10) not detectable in the absence of Eco SSB (lanes 2 and 9), at both 54° C. and 42° C. Taken together, these data show that the use of Eco SSB improves specificity and reduces the need for precision in choosing and controlling hybridization stringency in a PCR detection method, whether the determinant of stringency is hybridization temperature or amount of polynucleotide complementarity.

Additional studies were conducted on primers having regions of non-homology to the target sequence to determine the effect of Eco SSB on detection of the target sequence in a PCR detection method using primers having substantial complementarity. Hybridization reaction admixtures were prepared by the above-described methods and using Taq DNA polymerase, except that 100 ng of human genomic DNA was admixed with the primer pair pr 1A and pr 1B, or with the primer pair pr 2A and pr 2B, in the presence (lanes 2 and 4) or absence (lanes 1 and 3) of 250 ng of Eco SSB, and the prepared admixtures were subjected to the above PCR cycles with a 54° C. hybridization temperature. The results are shown in FIG. 4.

The two primer pairs have sequences that were derived from the human dihydrofolate reductase gene (DHFR), at exon 1 (pr 1A and pr 1B), or at exon 2 (pr 2A and pr 2B). However, each primer has 18 nucleotide residues at their 5' ends that are not homologous to the DHFR gene, but rather correspond in sequence to portions of a universal lambda primer. At the 3' end of each primer there is a stretch of 33 nucleotides (pr 1A), 27 nucleotides (pr 1B), 27 nucleotides (pr 2A), or 30 nucleotides (pr 2B) that correspond to portions of the human DHFR gene. Thus, when specifically hybridized to the human genomic DNA DHFR gene, the duplex containing these primers has a 5' "tail" region comprising 18 nucleotides that is not complementary or hybridized to the template and is attached to the remaining 3' portion comprising 27 to 33 nucleotides that is hybridized to the DHFR gene. The above DHFR primers are therefore examples of primers having substantial complementarity with the target sequence.

Figure 4:
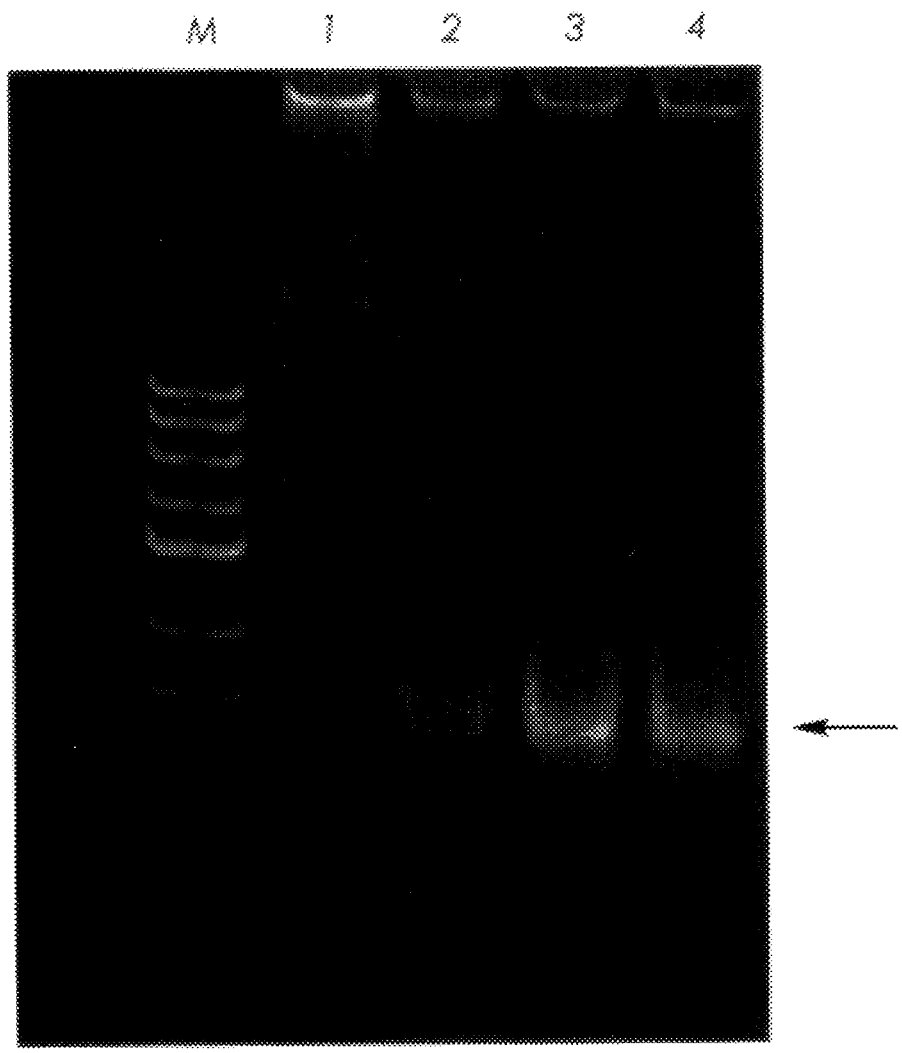
FIG. 4 illustrates the use of two different primer pairs in a PCR-based detection method, as described in Example 2, in which the primers have regions of non-homology with the specific target nucleic acid sequence. Primer extension products produced by PCR using the primer pair pr 1A and pr 1B (lanes 1 and 2) or using the primer pair pr 2A and pr 2B (lanes 3 and 4) were analyzed as described in FIG. 1, and using the same markers in lane M. PCR was conducted in the presence (lanes 2 and 4) or absence (lanes 1 and 3) of Eco SSB, and was directed at detecting the single copy DHFR gene present in human genomic DNA. The arrow indicates the position of the 250 bp band corresponding to a specifically amplified nucleic acid fragment, which is visible in lanes 2, 3 and 4, but not visible in lane 1.

As shown in FIG. 4, the two DHFR primer pairs pr 1A and pr 1B (lane 3) or pr 2A and pr 2B (lanes 1 and 2) detect a specific nucleic acid sequence by the PCR method that produces an amplified duplex DNA molecule of about 250 bp. Although the pr 2A and pr 2B primer pair yielded a specific band both in the presence or absence of Eco SSB (lanes 1 and 2), the pr 1A and pr 1B primer pair only yielded a specific band when Eco SSB was present (lane 3). Although the reason for this difference between the two primer pairs is not presently identified, an improvement in the PCR detection method was demonstrated by the data in FIG. 4 for one of the two primer pairs tested by including Eco SSB in the PCR method. These results therefore demonstrate that primers with substantial but not complete complementarity are effective for use in combination with an SSB protein in the presently disclosed PCR detection method.

The foregoing description and the examples illustrate the present invention but are not intended to limit the scope of the invention. Those skilled in the art recognize modifications and variations of the exemplified embodiments that are within the spirit and scope of the invention described and claimed herein.

What is claimed is:

1. A method of preparing a primed template, whereby nonspecific primer hybridization is reduced which method comprises:
   (a) forming a nucleic acid hybridization reaction admixture by admixing hybridization-effective amounts of (i) a primer nucleic acid which specifically hybridizes to a template nucleic acid to form a substrate for polynucleotide synthesis, (ii) said template nucleic acid, (iii) an isolated single-stranded nucleic acid binding protein, and (iv) a divalent cation; and
   (b) maintaining said nucleic acid hybridization reaction admixture under hybridizing conditions for a time period sufficient for said primer nucleic acid to specifically bind said template nucleic acid, thereby forming said primed template.

2. The method of claim 1 wherein single-stranded nucleic acid binding protein is selected from the group consisting of Eco SSB, T4 gene 32 protein, and T7 SSB.

3. The method of claim 1 wherein said single-stranded binding protein is Eco SSB.

4. The method of claim 1 wherein said divalent cation is selected from the group consisting of $Mg^{++}$, $Mn^{++}$, $Ca^{++}$ and $Zn^{++}$.

5. The method of claim 1 wherein said divalent cation is $Mg^{++}$.

6. The method of claim 1 wherein said hybridization-effective amount of divalent cation is in the range of 0.5 mM to 20 mM.

7. The method of claim 1 wherein said single-stranded nucleic acid binding protein is Eco SSB and said divalent cation is $Mg^{++}$ present at a concentration of about 15 mM.

8. The method of claim 1 wherein said hybridization-effective amount of single-stranded nucleic acid binding protein is in the range of 1 ng to 10 ug per 100 ng of template nucleic acid.

9. A method of preparing a primed template, whereby nonspecific primer hybridization is reduced, which method comprises:
   (a) forming a nucleic acid hybridization reaction admixture by mixing hybridization-effective amounts of (i) a primer nucleic acid which specifically hybridizes to a single-stranded template nucleic acid to form a substrate for polynucleotide synthesis, (ii) said single-stranded template nucleic acid, (iii) an isolated single-stranded nucleic acid binding protein, and (iv) a divalent cation; and
   (b) maintaining said nucleic acid hybridization reaction admixture under hybridizing conditions for a time period sufficient for said primer nucleic acid to specifically bind said template nucleic acid, thereby forming said primed template.

10. The method of claim 9 wherein said single-stranded nucleic acid binding protein is selected from the group consisting of Eco SSB, T4 gene 32 protein and T7 SSB.

11. The method of claim 9 wherein said single-stranded binding protein is Eco SSB.

12. The method of claim 9 wherein said divalent cation is selected from the group consisting of $M^{++}$, $Mn^{++}$, $Ca^{++}$ and $Zn^{++}$.

13. The method of claim 9 wherein said divalent cation is $Mg^{++}$.

14. The method of claim 9 wherein said hybridization-effective amount of divalent cation is in the range of 0.5 mM to 20 mM.

15. The method of claim 9 wherein said single-stranded nucleic acid binding protein is Eco SSB and said divalent cation is $Mg^{++}$ present at a concentration of about 15 mM.

16. The method of claim 9 wherein said hybridization-effective amount of single-stranded nucleic acid binding protein is in the range of 1 ng to 10 ug per 100 ng of template nucleic acid.

* * * * *

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
( A ) LENGTH: 26 base pairs
( B ) TYPE: nucleic acid
( C ) STRANDEDNESS: unknown
( D ) TOPOLOGY: unknown ( i i ) MOLECULE TYPE: DNA ( x i ) SEQUENCE DESCRIPTION: SEQ ID NO:1:

TCTGGCTCCA GCCAAAGCCA CCCTAG 26

( 2 ) INFORMATION FOR SEQ ID NO:2:

( i ) SEQUENCE CHARACTERISTICS:
( A ) LENGTH: 26 base pairs
( B ) TYPE: nucleic acid
( C ) STRANDEDNESS: unknown
( D ) TOPOLOGY: unknown ( i i ) MOLECULE TYPE: DNA ( x i ) SEQUENCE DESCRIPTION: SEQ ID NO:2:

GGCTGAGCCC AGTGCCTCCT TGAGTA 26

( 2 ) INFORMATION FOR SEQ ID NO:3:

( i ) SEQUENCE CHARACTERISTICS:
( A ) LENGTH: 23 base pairs
( B ) TYPE: nucleic acid
( C ) STRANDEDNESS: unknown
( D ) TOPOLOGY: unknown ( i i ) MOLECULE TYPE: DNA ( x i ) SEQUENCE DESCRIPTION: SEQ ID NO:3:

GGTGGCGACG ACTCCTGGAG CCC 23

( 2 ) INFORMATION FOR SEQ ID NO:4:

( i ) SEQUENCE CHARACTERISTICS:
( A ) LENGTH: 23 base pairs
( B ) TYPE: nucleic acid
( C ) STRANDEDNESS: unknown
( D ) TOPOLOGY: unknown ( i i ) MOLECULE TYPE: DNA ( x i ) SEQUENCE DESCRIPTION: SEQ ID NO:4:

GACAGTCACT CCGGCCCGTG CGG 23

( 2 ) INFORMATION FOR SEQ ID NO:5:

( i ) SEQUENCE CHARACTERISTICS:
( A ) LENGTH: 51 base pairs
( B ) TYPE: nucleic acid
( C ) STRANDEDNESS: unknown
( D ) TOPOLOGY: unknown ( i i ) MOLECULE TYPE: DNA ( x i ) SEQUENCE DESCRIPTION: SEQ ID NO:5:

TGTAAAACGA CGGCCAGTGG GGCGGCCACA ATTTCGCGCC AAACTTGACC G        51

( 2 ) INFORMATION FOR SEQ ID NO:6:

( i ) SEQUENCE CHARACTERISTICS:
        ( A ) LENGTH: 45 base pairs
        ( B ) TYPE: nucleic acid
        ( C ) STRANDEDNESS: unknown
        ( D ) TOPOLOGY: unknown ( i i ) MOLECULE TYPE: DNA ( x i ) SEQUENCE DESCRIPTION: SEQ ID NO:6:

CAGGAAACAG CTATGACCGT GGGCAGCCTG CGCCCGTTTG GGTCC        45

( 2 ) INFORMATION FOR SEQ ID NO:7:

( i ) SEQUENCE CHARACTERISTICS:
        ( A ) LENGTH: 45 base pairs
        ( B ) TYPE: nucleic acid
        ( C ) STRANDEDNESS: unknown
        ( D ) TOPOLOGY: unknown ( i i ) MOLECULE TYPE: DNA ( x i ) SEQUENCE DESCRIPTION: SEQ ID NO:7:

TGTAAAACGA CGGCCAGTCA AGGGATAATG TTTCGAACGC TGTTT        45

( 2 ) INFORMATION FOR SEQ ID NO:8:

( i ) SEQUENCE CHARACTERISTICS:
        ( A ) LENGTH: 48 base pairs
        ( B ) TYPE: nucleic acid
        ( C ) STRANDEDNESS: unknown
        ( D ) TOPOLOGY: unknown ( i i ) MOLECULE TYPE: DNA ( x i ) SEQUENCE DESCRIPTION: SEQ ID NO:8:

CAGGAAACAG CTATGACCCC CAGATTAACA CGGAAAACTT TCCATTTA        48

( 2 ) INFORMATION FOR SEQ ID NO:9:

( i ) SEQUENCE CHARACTERISTICS:
        ( A ) LENGTH: 18 base pairs
        ( B ) TYPE: nucleic acid
        ( C ) STRANDEDNESS: unknown
        ( D ) TOPOLOGY: unknown ( i i ) MOLECULE TYPE: DNA ( x i ) SEQUENCE DESCRIPTION: SEQ ID NO:9:

CGACGACTCG TGGAGCCC        18

( 2 ) INFORMATION FOR SEQ ID NO:10:

( i ) SEQUENCE CHARACTERISTICS:
        ( A ) LENGTH: 18 base pairs
        ( B ) TYPE: nucleic acid
        ( C ) STRANDEDNESS: unknown
        ( D ) TOPOLOGY: unknown ( i i ) MOLECULE TYPE: DNA ( x i ) SEQUENCE DESCRIPTION: SEQ ID NO:10:

GACAGTCACT CCGGCCCG        18